United States Patent
Helm et al.

(10) Patent No.: US 6,946,260 B2
(45) Date of Patent: Sep. 20, 2005

(54) ALLERGEN/INFLAMMATORY TESTING AND DIAGNOSIS

(75) Inventors: Birgit Anna Helm, Broomhall Park (GB); Anne Penelope Margaret Wilson, Anglesey (GB); Denise Moreira-Machado, Sheffield (GB)

(73) Assignee: Euro/DPC Limited, Gwynedd (GB)

( * ) Notice: Subject to any disclaimer, the term of this patent is extended or adjusted under 35 U.S.C. 154(b) by 0 days.

(21) Appl. No.: 09/133,766

(22) Filed: Aug. 12, 1998

(65) Prior Publication Data

US 2002/0187520 A1 Dec. 12, 2002

Related U.S. Application Data

(62) Division of application No. 08/446,760, filed as application No. PCT/GB93/02430 on Nov. 25, 1993, now abandoned.

(30) Foreign Application Priority Data

Nov. 28, 1992 (GB) ............................................ 92249564

(51) Int. Cl.⁷ ............................................... G01N 33/53
(52) U.S. Cl. ............................ 435/29; 435/2; 435/7.1; 435/7.2; 435/7.24; 435/325; 435/372; 435/353; 435/355; 436/201; 436/804; 436/811
(58) Field of Search ............................ 435/2, 7.1, 7.2, 435/7.24, 29, 325, 353, 355, 372; 436/501, 804, 811

(56) References Cited

U.S. PATENT DOCUMENTS 4,559,310 A * 12/1985 Cantor et al. ............... 436/519

OTHER PUBLICATIONS

Wilson et al., J. clin. Immunoassay, 16:91–95, 1993.*
Levi–Schaffer et al., Pharmacol. Res., 24:307–317, 1991.*
Gilfillan et al., J. Immunol., 149:2445–2451, 1992.*
Benyon et al., Br. J. Pharmacol., 97:898–904, 1989.*
Komisar et al., Inf. and Immunity, 60:2961–72, 1992.*
Bochner et al., New England J. Med., 324: 1785–1790, 1991.*

* cited by examiner

Primary Examiner—Ronald B. Schwadron
(74) Attorney, Agent, or Firm—Sughrue Mion, PLLC

(57) ABSTRACT

The invention relates to the use of a secretor variant cell-line expressing the alpha moiety of human IgE binding protein to determine the allergic status of a given individual. Moreover, the cell-line is also used to provide an assay system for determining the allergenicity of substances and for subsequently providing therapeutic compositions which render said substances ineffective. In addition, the invention also relates to the use of said cell-line to determine the IgE independent irritancy of substances and compositions effective for attenuating the effects of said substances.

8 Claims, 3 Drawing Sheets

Figure 5

| Clone | Ligand | $K_d$ (nM) | Receptors/cell ($\times 10^{-5}$) | $N$ |
|---|---|---|---|---|
| RBL-2H3 (I) | hIgE | nb | 0 | >10 |
|  | rIgE (A) | 14.0 +/- 0.4 | 10.6 +/- 0.7 | 3 |
|  | rIgE (B) | 13.5 +/- 0.2 | 10.7 +/- 0.8 | 2 |
| RBL-2H3 (H) | hIgE | nb | 0 | >10 |
|  | rIgE (A) | 12.7 +/- 0.4 | 8.3 +/- 0.5 | 3 |
|  | rIgE (B) | 13.8 +/- 0.7 | 8.1 +/- 0.6 | 2 |
| I 5/3/C | hIgE | 2.3 +/- 0.03 | 2.2 +/- 0.04 | 2 |
|  | rIgE | 15.1 +/- 0.9 | 17.3 +/- 0.4 | 2 |
| H 2/2/C | hIgE | 2.2 +/- 0.04 | 1.0 +/- 0.1 | 2 |
|  | rIgE | 10.4 +/- 0.5 | 11.0 +/- 0.6 | 2 |
| H 7/1/A | hIgE | 2.4 | 0.7 | 1 |
|  | rIgE | 14.0 +/- 0.6 | 0.1 +/- 0.6 | 2 |

Figure 6

| | Mediators Measured | | |
|---|---|---|---|
| Antigen | 5-HT | Protease | β-Hexosaminidase |
| Venoms, bee/wasp (1% suspensions) | ++++ | +++++ | ++++ |
| Phospholipase A2 (bee venom), 1μg/ml | + | + | + |
| Phospholipase C (*B.cereus*) | ++++ | ++++ | ND |
| House Dust Mite extracts, (freshly prepared) 1% suspensions | +++ | +++ | ND |
| House Dust Mite extracts, commercial sources, 1% suspensions | - | +/- | ND |
| Condom extract (1:400) (*Hevea brasiliensis*) | ++ | ++ | ND |
| Aspirin (25mg/ml) | +++ | +++ | ND |
| Influenza virus (5% suspension) | + | + | ND |
| Herpes simplex virus (5% suspension) | + | + | ND | ent.
ALLERGEN/INFLAMMATORY TESTING AND DIAGNOSIS

This is a divisional of application(s) Ser. No. 08/446,760 filed on Jul. 21, 1995 now abandoned which, in turn, is based on International Application PCT/GB93/02430 filed on Nov. 25, 1993 and which designated the U.S.

The invention relates to a method and test system for determining an individual's sensitivity to at least one pre-selected allergen/irritant and for determining the allergenicity or inflammatory characteristics of chemicals; further, the invention also relates to a therapeutic treatment for attenuating antigen-induced or inflammatory-induced mediator response to allergenic or inflammatory stimulation, respectively.

The response of an individual sensitive or responsive to a particular allergen or irritant is typically characterized by, amongst other things, an inflammatory response. This inflammatory response is produced as a result of the release of pharmacologically active mediators from mast cells and basophils. Indeed, a number of workers have shown that the use of mast cells and/or basophils cells in allergy testing is well established, for example, the following documents demonstrate sensitisation of these cells followed by exposure to allergen and the subsequent detection of a response, U.S. Pat. No. 4,559,310, EP 0 265 411, and U.S. Pat. No. 3,900,558. The activation of these cells in allergic responses such as asthma and hay fever is known to be mediated by the antibody IgE. It is known that there is a high-affinity receptor for IgE (FceR1) on the surface of mast cells and basophils, and further that me aggregation of IgE occupied receptors by antigen is responsible for the release of allergic mediators from such cells. Indeed, the use of cell-lines expressing this high affinity receptor have been used to determine the allergenicity of food additives, Japanese Journal of Toxicology and Environmental Health (1991) volume 37(5) 370–378. The FceR1 receptor is known to be made of at least three different sub units, alpha, beta and gamma. The alpha sub unit is known to bind IgE.

Investigators have successfully transfected the human FceR1 alpha sub unit into a rat mast cell-line RBL-2H3 thus producing a rat mast cell-line which is capable of expressing the human FceR1 alpha, Journal of Immunology (1992) volume 149(7) 2445–2451.

We have successfully transfected human FcerR1 alpha sub unit into a rat mast cell-line RBL-2H3 (deposited in accordance with The Budapest Treaty of 1977 with the European Collection of Animal Cell Cultures, Public Health Laboratories, Service, Centre For Applied Microbiology and Research, Porton Down, Salisbury, Wiltshire, FP4 OJG, UK, accession number 93112513, named RBL-2H3 H2/2/C), and the precise techniques which we used are described in detail in the following references: Conservation Of Signal Transduction Mechanisms Via The Human FceR1 Alpha After Transvection Into A Rat Mast Cell-Line RBL-2H3, Gilfillan, A. M., Kado-Fong H., Wiggan, G. A, Hakimi, J., Kent, U., and Kochan J. P., Journal of Immunology 149, 2445–2451 1992, Revisiting the Basophil Degranulation Test, Wilson, A. P. M., Moreira-Machado, D., Rhodes, N., Ahmad, T. B., Pullar C. E., and Helm, B. A., Journal of Clinical Immunoassay 16, 91–95 1993; and Human IgE mediates stimulus secretion coupling in rat basophilic leukemia cells transfected with the alpha chain of the human high-affinity receptor, Wilson A. P. M., Pullar C. E., Camp, A. M., and Helm, B. A., European Journal of Immunology 23, 240–244, 1993. The information and features described in these prior publications implicitly belong to the description of the invention contained in this application and thus to the content of this application. It is of note that such information and features contribute to achieving the technical aim of the invention, that is to provide a method and test system for determining sensitivity to an allergen or irritant and therapeutic treatments for attenuating same, and as such are comprising the solution of the technical problem underlying the invention which is the subject of this application. It follows that protection may be sought for such features described in these prior publications.

It has been found that this cell-line is a useful tool for understanding the fundamental steps involved in the above described response. However, we have used a high secretor variant of this cell-line to develop a method, and corresponding assay system, for determining the allergic/inflammatory status of an individual to a pre-selected allergen/irritant. Moreover, we have also used this cell-line for determining the potential allergen/irritancy of pre-selected chemicals. Further, the cell-line has been used to develop a therapeutic treatment for attenuating antigen-induced or inflammatory mediator response to allergenic or irritant stimulation.

Turning to the first method and corresponding assay system, it is known that individuals sensitive to a particular allergen have in their serum allergen specific IgE molecules, these are also known as sensitizing agents. This information has been used in the past to develop skin tests for the purpose of determining the allergen sensitivity of a given individual. However, these skin tests are potentially dangerous since they can have a booster effect in an already sensitized individual and in some countries such skin tests are illegal.

We have therefore used the afore described sector variant to develop a method which includes incubating the cell-line with serum from an individual to be tested and then challenging the cell-line with a pre-selected allergen.

It follows that if an individual's serum contains allergen specific IgE which corresponds to the allergen to be tested, the cell-line will respond in an immuno-reactive way and release pharmacologically active mediators. The detection of these mediators is therefore a means of determining whether an immunogenic reaction has taken place. This in turn signifies the allergic status of the individual.

According to a first aspect of the invention there is therefore provided a method for determining the allergic status of an individual comprising:
1. exposing a cell-line, which is a secretor variant of mast cell or basophil lineage and is transfected with a moiety capable of binding human IgE, to a sentising agent;
2. challenging the cell-line with at least one allergen; and
3. determining the release of mast cell or basophil mediators in response to said challenge.

In a preferred method of the invention the said sensitizing agent comprises human serum and more preferably human serum from the said individual, or alternatively, said sensitizing agent comprises human IgE or a functional equivalent thereof.

In a preferred method of the invention the mast cell-line is an RBL-2H3 cell-line but in any case the cell-line is transfected with a moiety capable of binding human IgE with high-affinity. Alternatively the cell-line is a secretor variant and is of mast cell or basophil lineage and is transfected with a moiety capable of binding human IgE.

Furthermore, ideally, the cell-line is first pre-incubated in a solution containing radio active, or other, marker, preferably histamine or tritiated 5-hydroxytryptamine [$^3$H]-5HT (1 uCi/ml) or $^{14}$C arachadonic acid ideally until equilibrium has taken place, then the cells are washed to remove traces of extra cellular radio activity. The cells are sensitized and challenged with allergen. At the end of the reaction the cellular environment in which the cell-line is located, that is supernatant, is assayed for the presence of radio active marker such as histamine or tritiated 5-hydroxytyptamine [$^3$H]-5HT or $^{14}$C arachadonic acid, thus indicating the release of same from said cells.

A commercially pretend method of the invention comprises the use of a spectrophotometric or colourimetric means for determining the release of mast cell mediators. For example, the release of cell mediators such as proteases is detected by including in the cellular environment, or supernatant, a chromogen that is acted upon by said proteases in such a way that a colour change is observed. However, it is within the scope of the invention to determine protease release by using any known proteolytic assay. Alternatively, it is within the scope of invention to determine mast cell or basophil cell action by measuring ionic fluctuations such as mobilization of intercellular calcium or membrane potential fluctuations.

In a further preferred method of the invention, cell mediator release is determined by the use of standard antibody binding assays which specifically identify a preselected cell mediator.

It will be understood that the determination of a reaction can be undertaken by determining the release of any preselected mast cell mediator, for example, one could assay for the presence of interleukins such as interleukin 3, 4, 5 6, and 8.

According to a further feature of this aspect of the invention, there is provided an assay kit for determining the allergen sensitivity of an individual comprising:
1. a cell-line which is a secretor variant of a mast cell-line or a basophil cell-line and is transfected with a moiety capable of binding human IgE;
2. test allergen; and
3. means necessary to determine the absence or presence of an immune response.

In a preferred embodiment of the invention the cell-line is an RBL-2H3 cell-line but in any case the cell-line is transfected the alpha-chain of the human high-affinity receptor for IgE. Alternatively, the cell-line is a secretor variant of a human mast cell-line or human basophil cell-line expressing moieties which bind human IgE with high-affinity.

Further, the preferred means comprise either an amount of radio active marker and ideally a radio active marker such as, but not limited to, tritiated 5-hydroxytryptamine or $^{14}$C arachadonic acid.

Ideally the means is a chromogen or alternatively a means of measuring proteolytic activity or alternatively an assay means.

We have also developed the use of a mast cell or basophil cell-line to determine the potential allergenicity of a given chemical.

It is known that some chemicals can give rise to an inflammatory response which appears to be IgE independent. Such chemicals include bee and vespid venoms (the causative agents identified from these sources are basic proteins like mellitin and mastopran, phospholipase A, cysteine and serine protease, a number of lectins, including viral haemagluttinins that interact with carbohydrate residues on the receptor and/or IgE, and sulfiting agents (food preservatives).

Using the invention we have determined that the following chemicals elicit the release of mast cell mediators from our cell-lines and would therefore seem to give rise to an inflammatory response which is IgE independent. These chemicals include bacterial phospholipase C (B cereus), house dust mite proteins, salicylates (aspirin based drugs), latex suspensions, extract from manufactured latex products (gloves, condoms) and spermicide.

The mechanism by which these chemicals induce mast cell exocytosis in the absence of IgE has yet to be elucidated, however, the fact that this effect occurs means that a mast cell or basophil cell-line can be used to determine the potential allergenicity of chemicals by exposing the cell-line to chemicals and determining the absence or presence of a reaction by determining mast cell exocytosis or mediator release.

According to a second aspect of the invention there is therefore provided a method for determining the potential irritancy of a pre-selected substance comprising:
1. exposing a mast cell-line and/or basophil call-line to a pre-selected amount of said substance; and
2. then determining the release of mast cell and/or basophil cell-mediators in response to said exposure.

In a preferred method of the invention the mast cell-line is a secretor variant of a cell-line such as a RBL-2H3 cell-line which may or may not be transfected with a moiety capable of binding human IgE with high-affinity. In a preferred method of the invention and especially where the substance to be tested reacts with a cell bound immunoglobulin of IgE isotype the mast cell-line or basophil cell-fine is also exposed to an amount of IgE or a functional equivalent thereof. In this case, where the mast cell-line or basophil cell-line is incubated with IgE, it is preferable to use the transfected RBL-2H3 cell-line, or a human cell-line. Further, in a preferred embodiment, the mast cell-line is pre-incubated with radio active marker and ideally histamine or 5-hydroxtryptamine or $^{14}$C arachadonic acid, ideally until equilibrium has taken place, and then the cells are washed to move any extra cellular radio active or tritiated substances. The cells are then exposed to the said chemical and the cellular environment is then preferably assayed for the presence of radio active marker such as tritiated histamine thus indicating the release of same from said cells.

In a yet further preferred embodiment of the invention the cell-line is exposed to a chromogen which changes colour as a result of the presence of a reaction.

In a yet further preferred embodiment of the invention the release of cell mediators is determined using standard proteolytic assays or antibody assays as described above. Or, alternatively, by monitoring transmembrane or intracellular ion fluxes.

We have further used the cell-line to identify therapeutic compositions for attenuating antigen-induced or irritant-induced mediator response to allergenic stimulations or irritants. We have found that many of the primary effects of both chemical- or irritant-induced mediator release from mast cell-lines and basophil cell-lines and IgE mediated, antigen-induced mediator release from mast cell-lines and basophil cell-lines can be attenuated by selective substrates or inhibitors for mast cell and basophil derived proteolytic enzymes. Such substrates or inhibitors may inhibit triggering of target cells but will also inhibit the secondary activation which is probably due to the release of mast cell and basophil proteases. We have also found that similarly, competing sugars, (which were identified on the basis of proteins that interact with carbohydrate residues on either IgE or cells expressing cellular receptors) such as N-acetyl-D-glucosamin, a-methyl-mannoside, N-acetyl neuraminic acid, b-D-galactose, a-L-fucose, and lactose can inhibit the triggering of mast cells and basophils by interaction with lectins present in, for example, pollen or bacterial and viral agglutinins.

We have therefore successfully identified a number of substances which may be called antagonists and which may be responsible for inhibiting the activation of a mast cell-line or basophil cell-line.

According to a yet further aspect of the invention there is therefore provided a therapeutic composition comprising a substance containing a C-terminal lysine or arginine residue for the treatment of an allergic reaction.

According to a yet further aspect of the invention there is provided a therapeutic composition comprising a substrate or inhibitor, competitive or otherwise, of mast cell or basophil proteases for the treatment of an allergic reaction.

According to a yet further aspect of the invention there is provided a further therapeutic composition comprising a competing sugar that interacts with carbohydrate residues on either IgE or cells expressing lectin binding moieties for the treatment of an allergenic reaction.

In a preferred embodiment the sugar comprises N-actetyl-D-glucosamin or a-methyl-mannoside or N-acetyl neuraminic acid or b-D-galactose or a-L-fucose or lactose or other biologically active derivatives.

An embodiment of the invention will now be described by way of example only.

Figure 1:
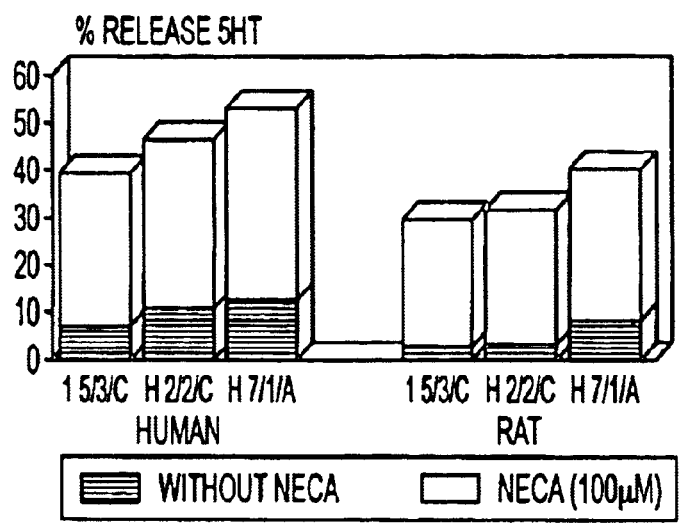
FIG. 1

Histogram of the release of 5-hydroxytryptamine (5HT) from transfected cell-lines. Clones were incubated for 24 hours at 37 degrees C. with Dex, o-nitrophenol (DNP)-specific rat IgE or 4-hydroxy-3-nitrophenacetyl caproic acid (NIP)-specific human IgE (hIgE) in the presence of Dexamethasone (Dex) ($10^{-8}$M) and [$^3$H]-5HT. Cross-linking of receptor occupied IgE was effected with either DNP or NIP linked to serum albumin (HSA in the presence and absence of 5'(N-ethylcarboxyamindo)-adenosine (NECA) (100 $\mu$M). [$^3$H]-5HT was measured after a 15 minutes incubation period and release was corrected for background and expressed relative to the total tritiated [$^3$H]-5HT incorporated.

FIG. 2

A comparison of the release of [$^3$H]-5HT and β-hexosaminidase. Transfected cells (H 2/2/C) were incubated with Dex ($10^{-6}$M), NIP-specific hIgE (1 $\mu$g/mL) and, where appropriate, [$^3$H]-5HT for 24 hours at 37 degrees C. The cells were washed and triggered with NIP-HSA in the presence of NECA (100 $\mu$M). The release of pre-loaded [$^3$H]-5HT (●) and endogenous β-hexosaminidase (○) were assessed. Each value is the mean of two tests; release was corrected for background.

FIG. 3

Triggering of RBL-2H3 (H 2/2/C) transfectants following sensitization with serum from a bee-venom-allergic individual. Cells were incubated with the serum (1:10), Dex ($10^{-6}$M) and [$^3$H]-5HT. After washing and pre-incubation the cells were challenged with a range of concentrations of purified bee venom phospholipase $A_2$ (PLA$_2$). The percentage release of [$^3$H]-5HT (●) and β-hexosaminidase (○) were determined; data were corrected for background and normalized with respect to values obtained for triggering with hIgE-DNP (1 $\mu$g/mL and NIP-HSA (100 ng/mL).

FIG. 4

Transfected RBL-2H3 clones were incubated for 24 hours with or without serum (1:10 dilution) from a bee venom sensitive individual (EC) in the presence of $10^{-6}$M dexamethazone and [$^3$H]-5-hydroxytryptamine. After washing, cells were challenged with antigen in the presence of 100 $\mu$M 5' (N-ethylcarboxyamido)-adenosine (NECA).

[$^3$H]-5-Hydroxytyptamine was measured after a 15 minutes incubation period, release was corrected for background and expressed relative to the total [$^3$H]-5-hydroxytryptamine incorporated. For experimental details see Wilson, A. P. M., Pullar, C. E. Camp, A. M., and Helm, B. A, Human IgE Mediates Stimulus Secretion Coupling in Rat Basophilic Leukemia Cells Transfected with the Alpha Chain of the Human High-Affinity Receptor, European Journal of immunology, 23:240–244, 1993, or alternatively, please see other references cited on Page 2 of this application.

FIG. 5

Parameters for the binding of iodinated [$^{125}$I] rat and human IgE to parental and transfected clones.

Clone were plated at $5\times10^4$ cells/well and incubated with Dex ($10^{-6}$M) for 24 hours at 37 degrees C. Parental cell-lines (RBL-2H3 intermediate secretors (I) and high secretors (H)) were incubated in the absence (A) and presence (B) of the steroid. Cells were incubated with a range of concentration of [$^{125}$I] labelled rat or hIgE in the presence and absence of a 50–100-fold excess of unlabelled ligand (for experimental details see Wilson, A. P. M., Pullar, C. E., Camp, A. M., and Helm, B. A., Human IgE Mediates Stimulus Secretion Coupling in Rat Basophilic Leukemia Cells Transfected with the Alpha Chain of the Human High-Affinity Receptor, European Journal of Immunology, 23:240–244, 1993, or alternatively, please see other references cited on Page 2 of this application). Before counting, cells were washed and lysed, and the data were analyzed by the method of Scatchard.

nb=non binder; N=number of determinations

FIG. 6

Antigen-induced mast cell mediator release from RBL-2H3 cells in the absence of sensitization with antigen-specific IgE.

Parent RBL-2H3 cells or clones transfected with the α-chain of the human high-affinity receptor complex were plated out in 24-well plates at $2\times10^5$ cells/well as described previously in the citations referred to on Page 2 of this application. For the determination of antigen-induced mediator release, plates were incubated at 37 degrees C. for 15 minutes, cooled on ice, the supernatant was removed, spun at 200×g (1 minute) before liquid scintillation counting to measure [$^3$H]-5-hydroxytryptamine (5-HT release. The ImmunoTech histamine enzyme immunoassay was used to quantify histamine release, and hydrolysis of toluene sulphonyl methyl ester was employed to monitor protease release (please see Wilson, A. P. M., Pullar, C. E., Camp, A. M., and Helm B. A., Human IgE Mediates Stimulus Secretion Coupling in Rat Basophilic Leukemia Cells Transfected with the Alpha Chain of the Human High-Affinity Receptor, European Journal of Immunology, 23:240–244, 1993, or alternatively, please see other references cited on Page 2 of this application).

| | |
|---|---|
| + | 3–8% mediator release |
| ++ | 8–15% mediator release |
| +++ | 15–25% mediator release |
| ++++ | 25–45% mediator release |
| ND | Not Determined |

EXAMPLE 1

A method and corresponding assay system for determining the allergenic of a given individual.

$2 \times 10^5$ cells of RBL-2H3 transfected with the α-chain of the human high-affinity receptor for IgE were placed in at least one test well and incubated in a total reaction volume of 0.4 ml buffer A or 24 hours at 37 degrees C. with tritiated 5HT (1 uCi/ml), in the presence of serum from an individual to be tested, a 2–100 fold dilution of human serum was used. (This serum may or may not contain antigen specific IgE corresponding to the allergen in the test method/kit depending upon the allergenic status of the individual.)

Following incubation, the cells were washed (2×1 ml) with buffer A (120 mM NaCl, 5 mM KCl, 25 mM PIPES, 1 mM $CaCl_2$, 0.04 mM $MgCl_2$, 5.6 mM glucose, 0.1% BSA, pH7.4) and pre-incubated for a period of 10 minutes at 37 degrees C. with buffer A (0.5 ml) which was before challenge with buffer A (0.4 ml) supplemented with the antigen in an amount of nanogram, microgram or milligram concentrations depending on the efficacy of the antigen source.

For the determination of antigen induced [$^3$H]-5HT release, the well was incubated at 37 degrees C. for 15 minutes, cooled on ice, supernatant was then removed and spun at 2000 g (1 minute) before liquid scintillation counting (2 minutes). The percentage release of [$^3$H]-5HT was calculated by the method of Siraganian and Hook (Manual of Clinical Immunology of the American Society for Microbiology Washington D.C., 1980 Page 808). Histamine release was demonstrated employing the ImmunoTech histamine immunoassay kit.

(We have also determined the release of proteases from this cell-line and this was analyzed by the method of Hummel [Homodified Spectrophotometric Determination of Chymotrypsin, Trypsin & Thrombin, Canadian Journal of Biochem Physiol Volume 37, Page 1959].)

As mentioned, the ability of high-secretor variant clones to support mediator release through receptor-bound human IgE was determined either by pre-loading the cells with [$^3$H]-5HT or by measuring the release of endogenous β-hexosaminidase. Briefly cells were plated out and Incubated for 24 hours at 37 degrees C., with [$^3$H]-5HT (if appropriate). Dex, o-dinitrophenol-(DNP-) specific rat IgE or 4p-hydroxy-3-nitrophenacetyl caproic acid-(NIP-) specific hIgE. The cells were washed with buffer A, pre-incubated for 10 minutes at 37 degrees C. with the same buffer and challenged, in fresh buffer, with either DNP-HSA (DNP conjugated to human serum albumin) 50 ng/ml or NIP-HSA 10 ng/ml in the presence of the adenosine analogue 5' (N-ethylcarboxyamido)-adenosine (NECA) 100 μM.

Properties of the Transfected Line

Following electroportation, transfection frequencies of $30 \times 10^{-6}$ and $1.5 \times 10^{-6}$ were obtained for RBL-2H3 intermediate secretors (I) and RBL-2H3 high secretors (H), respectively. On the basis of hFceR1α expression, three clones, namely I 5/3/C, H 2/2/C and H 7/1/A, were selected for further studies. FIG. 5 shows the relative number of receptors, following induction with Dex, demonstrating rat IgE and human IgE binding; rat IgE binds to the humanized receptor but with a 10-fold lower affinity than the natural ligand. As the interaction of hIgE with its receptor is an order of magnitude higher than the interaction of rat IgE with its receptor, the net result is that rat IgE engages hFceR1α with the same affinity as the rodent receptor. In addition to the data in FIG. 5, the rates of association and dissociation of rat and hIgE with I 5/3/C and rat IgE with the parental line RBL-2H3 (I), and the $K_d$ values calculated from these on/off rates were consistent with published data.

A feature of this application is the ability of the transfected cell-line to support mediator release in response to cross-linking receptor-associated hIgE. Significant release required the presence of NECA (100 μM, at the cross-linking stage, in order to counteract the effect of Dex. This steroid decreases antigen-induced cell secretion but increases the responsiveness to NECA. It has been suggested that Dex down-regulates the expression of the G protein $G_{αz}$ that may play a role in coupling the FceR1 complex to effector systems involved in mast cell exocytosis. FIG. 1 shows the release of 5HT from transfected cell-lines following priming with either rat or human IgE and clearly demonstrates the effect of NECA. Simulation through hFceR1α gave consistently higher release than when degranulation was effected through the native rodent receptor complex.

Figure 2:
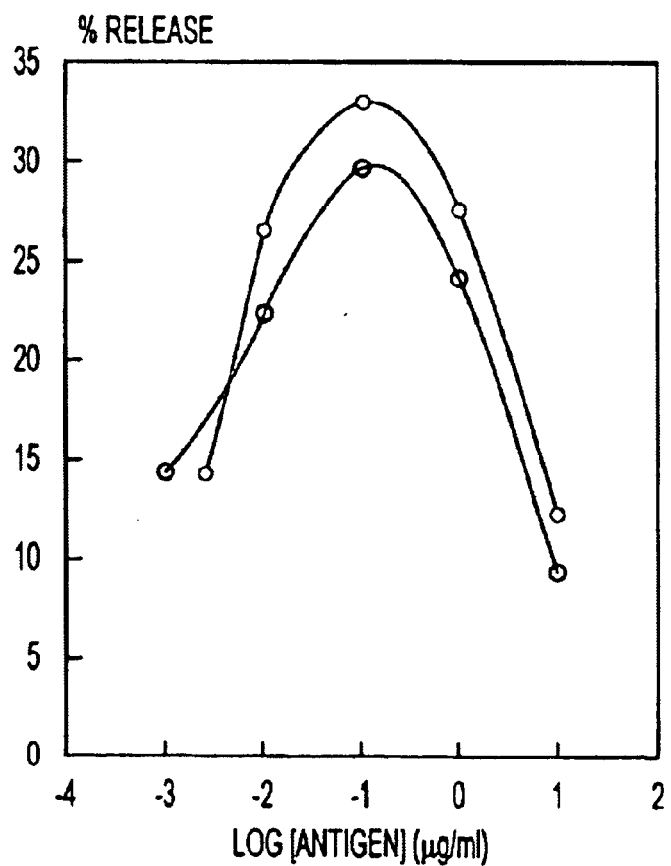

FIG. 2 shows a comparison between the release of β-hexosaminidase and preloaded [$^3$H]-5HT from H 2/2/C following hIgE-mediated, antigen-induced degranulation. The two assay systems compare reasonably well, although the former consistently yields lower values (7–10%) than [$^3$H]-5HT measurements.

Figure 3:
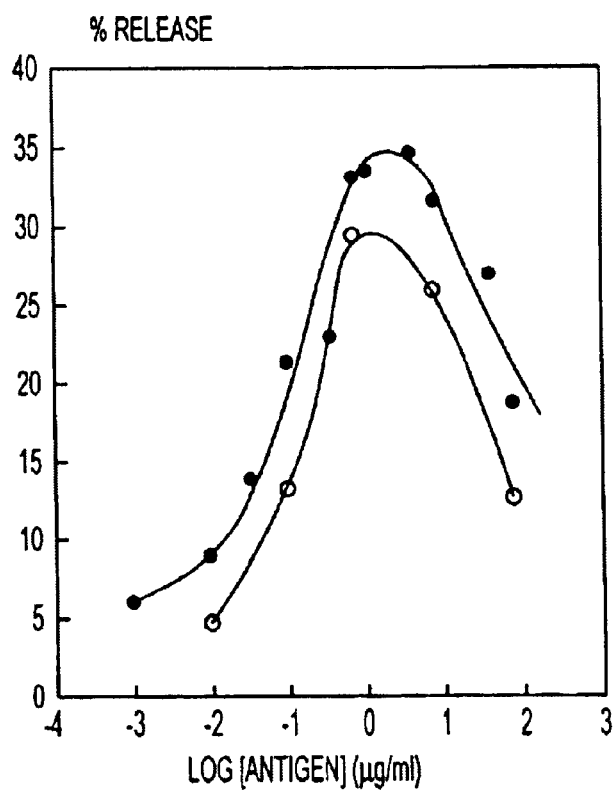

An example of the use of the transfected cell-line for the measurement of antigen-specific IgE is shown in FIG. 3. clone H 2/2/C was incubated with serum from a bee-venom-sensitive individual (EC) and challenged with bee venom $PLA_2$. A typical bell-shaped dose response curve for the release of β-hexosaminidase and [$^3$H]-5HT was observed when the IgE sensitized cell-line was challenged with increasing concentrations of $PLA_2$. Again the percentage release of β-hexosaminidase was less than that observed for [$^3$H]-5HT.

These results thus illustrate that the cell-line we have developed can be used, as we alone have realized, for the provision of a method and an assay system which can detect the allergenic status of an individual.

EXAMPLE 2

A method and corresponding essay system for detecting the potential irritancy or allergenicity of chemicals.

$2 \times 10^5$ cells of the RBL-2H3 cell-line transfected with the α-chain of the human high-affinity receptor for IgE were placed in at least one incubator well and incubated in a total volume of 0.4 ml of buffer A. (120 mM NaCl, 5 mM KCl, 25 mM PIPES, 1 mM $CaCl_2$, 0.04 mM $MgCl_2$, 5.6 mM glucose, 0.1% BSA, pH7.4) for 24 hours at 37 degrees C. with [$^3$H]-5HT (1 uCl/ml). (In this instance, in the presence of human serum and therefore in the presence of any antigen specific IgE.)

Following incubation, the cells were washed (2×1 ml) with buffer A and pre-incubated for a period of 10 minutes at 37 degrees C. with buffer A (0.5 ml) which was removed before challenge with buffer A (0.4 ml) supplemented with the irritant or antigen. The amount of irritant or antigen was in the range of nanograms, micrograms or milligram depending on the efficacy of the irritant source.

For the determination of irritant or antigen induced [$^3$H]-5HT release, the well was incubated at 37 degrees C. for 15 minutes, cooled in ice, supernatant was then removed and spun at 2000 g (1 minute) before liquid scintillation counting (2 minutes). The percentage release of [$^3$H]-5HT was calculated by the method of Siraganian and Hook. Histamine release was demonstrated employing the ImmunoTech histamine immunoassay kit.

(We have also determined the release of proteases from this cell-line and this was analysed by the method of Hummel)

Figure 4:
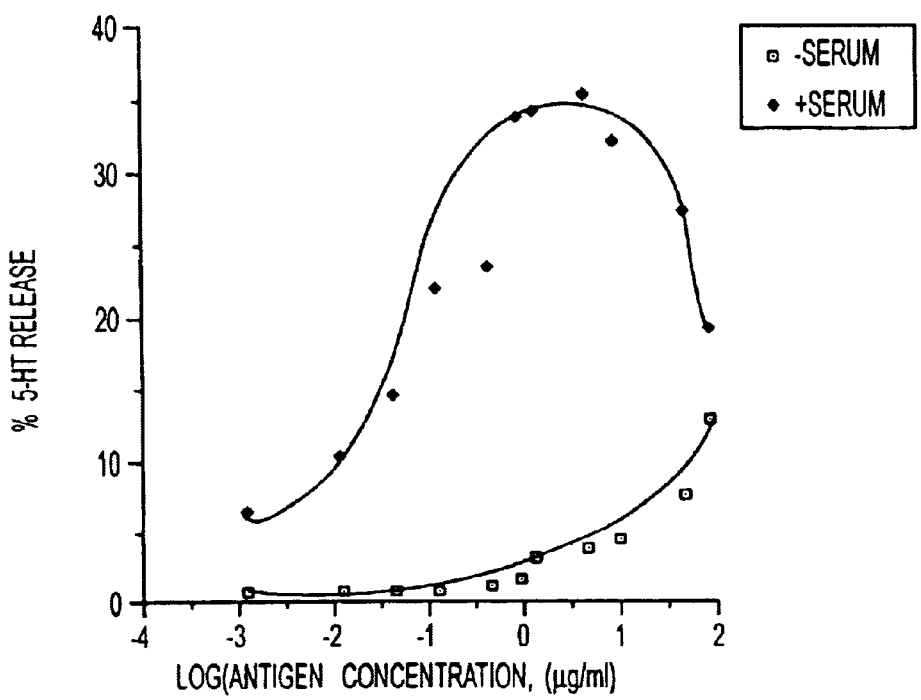

When the transfected cells were sensitized with the serum from a bee venom phospholipase $A_2$ sensitive individual (EC), mediator release could be demonstrated following challenge wit purified bee venom phospholipase $A_2$ (mellitin free). A typical bell-shaped dose response pattern was observed when the sensitized cells were challenged with increasing doses of antigen. Control experiments, where non-sensitized cells had been incubated with the same concentration of antigen in the absence of sensitizing serum also showed degranulation of mediators, but this time mediator release increased in response to antigen concentration (see FIG. 4)

Employing this cell-line, we were able to demonstrate that even in the absence of IgE several well defined allergens, (which in susceptible individuals give rise to an IgE response following the initial encounter) such as bee and vespid proteins, phospholipases, proteases from house dust mites and fungal spores, lectins present in pollen and grain, latex-associated products and spermicides, and aspirin based drugs can trigger the release of substantial levels of mediators of the allergic response from these calls (see FIG. 6).

The above results indicate that, as we have realized, our cell-line can be used for determining the potential irritancy or allergenicity of a chemical or substance.

EXAMPLE 3

In the development of a therapeutic composition for attenuating antigen-induced mediator response to allergenic stimulation the following method was used.

$2 \times 10^5$ cells of the RBL-2H3 cell-line transfected with the α-chain of the human high-affinity receptor for IgE were placed in at least one incubation well in a total reaction volume of 0.4 ml of buffer for 24 hours at 37 degrees C. with [$^3$H]-5HT (1 uCl/ml), in either the presence or absence of antigen specific IgE, that is either in the presence or absence of human serum (as above described) depending upon the nature of the allergic reaction to be attenuated. For example, where a composition was being tested or developed for its ability to attenuate an IgE mediated response such as asthma or hay fever, antigen specific IgE would be present, for example, in the form of human serum.

Following incubation, cells were washed (2×1 ml) with buffer A (120 mM NaC1, 5 mM KC1, 25 mM PIPES, 1 mM $CaCl_2$, 0.04 mM $MgCl_2$, 5.6 mM glucose, 0.1% BSA, pH7.4) and pre-incubated for a further period of 10 minutes at 37 degrees C. with buffer A (0.5 ml) which was removed before challenge with buffer A (0.4 ml) supplemented with a pre-selected antigen (in an amount as afore described) and the therapeutic composition or the antagonist.

For the determination of antigen induced [$^3$H]-5HT release, the well was incubated at 37 degrees C. for 15 minutes, cooled on ice, supernatant was then removed and spun at 2000 g (1 minute) before liquid scintillation counting (2 minutes). The percentage release of [$^3$H]-5HT was calculated by the method of Siraganian and Hook. Histamine release was demonstrated employing the ImmunoTech histamine immunoassay kit.

(We have also determined the release of proteases from this cell-line and this was analysed by the method of Hummel).

In the instance where therapeutic composition acted as an effective blocker of the antigen-induced allergic response, there was a significant reduction in [$^3$H]-5HT release.

Activated mast cells and basophils also secrete at least three proteases, the physiological function of which is unknown. These enzymes are serine endoproteases with a trypsin-like specificity. We have recently shown that after secretion following an immunological or non-immunological stimulus, proteases released from the activated RBL cell-line can induce mediator secretion from cells of their kind. This secondary burst of the release of inflammatory mediators can be attenuated by the inclusion of protease inhibitors or substrates for serine proteases like the synthetic substrate p-toluenesulphonyl-L-arginine methyl ester (TAME) or the human IgE-derived pentapeptide (HEPP) in the medium bathing the cells. This observation provides a self-evident explanation for the observed therapeutic effect of administration of HEPP to patients suffering from eg allergic rhinitis, initially attributed to be due to competitive inhibition of the IgE/FceR1 interaction, but later held untenable.

It will be understood that the therapeutic composition identified using the above method may be manufactured in any saleable from such as a pill, capsule, lozenge, tablets, medicine infusion, ointment nasal spray, inhalant or any other known means of manufacturing a medicament.

It will be understood that although the examples have been described by reference to an immuno-radioactive method, it is within the scope of the invention to d ploy a colourimetric technique, or proteolytic assay, or immunological assay, or antibody assay, or indeed any other standard technique of assay such as a measurement of membrane potential for determining the response of a mast cell-line or basophil cell-line to a given allergen or antagonist under the above specified conditions.

What is claimed is:

1. A method of assaying for potential allergenicity of a pre-selected substance or chemical comprising:

(a) exposing a mast cell-line and/or basophil cell-line to said substance or chemical in the absence of IgE specific for said substance or chemical;

(b) detecting release of at least one mast cell and/or basophil cell mediator in response to said exposing; and (c) designating the pre-selected substance or chemical as potentially allergenic based on detecting release of said at least one mast cell and/or basophil cell mediator.

2. The method according to claim 1, wherein said cell-line is a secretor variant of RBL-2H3.

3. The method according to claim 1, wherein said cell-line is pre-incubated with a marker.

4. The method according to claim 3, wherein the marker is tritiated 5-hydroxytryptamine, or histamine or β-hexoseaminidase.

5. The method according to claim 3, wherein the marker is $^{14}$C arachadonic acid.

6. The method according to claim 1, wherein the release of at least one mast cell and/or basophil cell mediator is detected using a chromogen which changes color in the presence of at least one mast cell and/or basophil cell mediator.

7. The method according to claim 1, wherein the release of at least one mast cell and/or basophil cell mediator is detected using an antibody binding assay.

8. The method according to claim 1, wherein said cell-line is transfected with a moiety capable of binding human IgE.

* * * * *